(12) United States Patent
Wang et al.

(10) Patent No.: US 8,031,930 B2
(45) Date of Patent: Oct. 4, 2011

(54) TESTING SYSTEM AND TESTING METHOD FOR INSPECTING ELECTONIC DEVICES

(75) Inventors: Bily Wang, Hsinchu (TW); Kuei-Pao Chen, Hsin Chu (TW); Hsin-Cheng Chen, Jhudong Township, Hsinchu County (TW); Ming-Hao Chou, Hsinchu (TW)

(73) Assignee: Youngtek Electronics Corporation, Hsinchu (TW)

( * ) Notice: Subject to any disclaimer, the term of this patent is extended or adjusted under 35 U.S.C. 154(b) by 565 days.

(21) Appl. No.: 12/285,184

(22) Filed: Sep. 30, 2008

(65) Prior Publication Data
US 2009/0251815 A1    Oct. 8, 2009

(30) Foreign Application Priority Data
Apr. 7, 2008    (TW) ............................... 97112481 A

(51) Int. Cl.
*G06K 9/00*    (2006.01)
(52) U.S. Cl. .................... 382/141; 382/145; 382/152
(58) Field of Classification Search ........... 382/141–152
See application file for complete search history.

(56) References Cited

U.S. PATENT DOCUMENTS

| 3,651,937 | A | * | 3/1972 | Kronseder | 209/524 |
| 3,716,136 | A | * | 2/1973 | Birner et al. | 209/525 |
| 4,691,231 | A | * | 9/1987 | Fitzmorris et al. | 348/127 |
| 5,721,386 | A | * | 2/1998 | Marette | 73/865.8 |
| 7,261,197 | B2 | * | 8/2007 | Nickey et al. | 198/346.2 |
| 7,438,192 | B1 | * | 10/2008 | Kohler et al. | 209/523 |

* cited by examiner

*Primary Examiner* — Gregory J Toatley
*Assistant Examiner* — Jarreas C Underwood
(74) *Attorney, Agent, or Firm* — Rosenberg, Klein & Lee

(57) ABSTRACT

A testing system for inspecting electronic devices includes a first transparent disk, a first image capturing unit disposed under the first transparent disk, a second disk disposed next to the first transparent disk, a guiding unit disposed on adjacent area between the transparent disk and the second disk, and a plurality of second image capturing units disposed around the second disk. A plurality of electronic devices is continuingly supplied onto the first transparent disk and the first image capturing unit is used for capturing the images of the bottom surfaces of the electronic devices. Then, the electronic devices are guided to the second disk via the guiding unit and the second image capturing units are used for capturing the images of other surfaces of the electronic devices. A testing method for electronic devices is further disclosed.

17 Claims, 5 Drawing Sheets

TESTING SYSTEM AND TESTING METHOD FOR INSPECTING ELECTONIC DEVICES

BACKGROUND OF THE INVENTION

1. Field of the Invention

The present invention relates to a testing system and a testing method for inspecting electronic devices. The invention in particular relates to a testing system having two disks which are used for inspecting the images of each of the electronic device's surface.

2. Description of Related Art

Mobile communication and electronic devices have been developed to be multi-functional, miniaturized, highly reliable and low cost. Therefore, different functions of circuit designs are integrated onto increasingly smaller chip size. For example, mobile phones with only voice communication function are out of date and newly designed phones commonly have many accessory functions, such that people can record important matters in the phone, transfer a text message to a friend or watch digital TV on the phone.

Take another example; electronic devices for cars represent highly sophisticated technologies such as navigation computer, global positioning system, and intelligence voice activation system. Accordingly with the development of automobile's electronics, the variety of electronic utilized by an automobile also increases.

Thus, with the increasing variety and sophistication of electronic devices, the quality and the reliability of the electronic components are crucial to the performance of the electronic devices. Generally, it is necessary for the components to be tested when the manufacturing procedure is finished. In the traditional inspection method, all the components are disposed on a large-area disk and many cameras are used for capturing the images of the components' surface appearance. For inspecting the bottom surface of each component, the large-area disk has to be transparent. One method is using a quartz glass as the large-area disk but quartz glass is an expensive material. In other words, the cost of the inspection system is extremely high. Another method is using a tempered glass as the disk. However, the hardness of the tempered glass is lower than that of the electronic components so that the surface of the tempered glass is easily scratched by the components. The scratches on the tempered glass surface influence the captured bottom surface image and the analysis for the bottom surface images will not be precise. On the other hand, there are cameras disposed on both sides of the disk (i.e., top side and bottom side) and the images may be not be in focus because of influence of light (i.e. glare or reflection) that passes though the large-area disk.

Therefore, in view of this, the inventor proposes the present invention to overcome the above problems based on his expert experience and deliberate research.

SUMMARY OF THE INVENTION

The primary object of the present invention is to provide for a testing system having two rotatable disks and the transparent and smaller of the two disks (a.k.a. small size disk or transparent disk) is used for inspecting the bottom surface of the electronic device.

The further object of the present invention is to improve the precision of testing system analysis. The small size disk is made by quartz glass and the high degree of hardness can prevent the disk form being scratched. Therefore, the camera can capture images through a clear disk body without any scratch, wherein the scratch would have resulted in light scattering effect, and the analysis of the images of the electronic devices are thus more precise.

In order to achieve the above objects, the present invention provides a testing system for inspecting electronic devices, comprising: a first transparent disk, wherein the electronic devices are continuously supplied on the first transparent disk; a first image capturing unit disposed under the first transparent disk for capturing bottom images of the electronic devices; a second disk (i.e. the non-transparent and bigger of the two disks) disposed adjacently to the first transparent disk; a guiding unit disposed on the adjacent area between the first transparent disk and the second disk for transferring the electronic devices on the first transparent disk to the second disk; and a plurality of second image capturing units disposed around the second disk for capturing images of other surfaces (i.e. surfaces other than the bottom surface, such as front surface, rear surface, top surface, left surface, and right surface) of the electronic devices.

In order to achieve the above objects, the present invention provides a testing method for inspecting outlooks of electronic devices using a testing apparatus, the testing apparatus including a first transparent disk, a first image capturing unit, a second disk, a guiding unit, and a plurality of second image capturing units, the testing method comprising: (a). continuously providing the electronic devices onto the rotating first transparent disk; (b) capturing a bottom surface of each electrode device via the first image capturing unit; (c) transferring the electronic devices onto the rotating second disk; and (d) capturing images of other surfaces of the electronic devices via the second image capturing unit.

The small-sized transparent disk is made by material possessing high degree of hardness and the cost of the total testing system is reduced due to the two disk approach (a.k.a. the two-step inspection method) that reduced the overall transparent disk area used for inspection. On the other hard, the two-step inspection method can collect the "bad" electronic devices right after the bottom surface inspection so that it is not necessary to inspect the other five surfaces of the electronic devices if it is already determined that the electronic devices has a defected bottom surface. Therefore, the inspection efficiency is improved.

In order to better understand the characteristics and technical contents of the present invention, a detailed description thereof will be made with reference to accompanying drawings. However, it should be understood that the drawings and the description are illustrative only and are not used to limit the scope of the present invention.

DETAILED DESCRIPTION OF PREFERRED EMBODIMENTS

Figure 1:
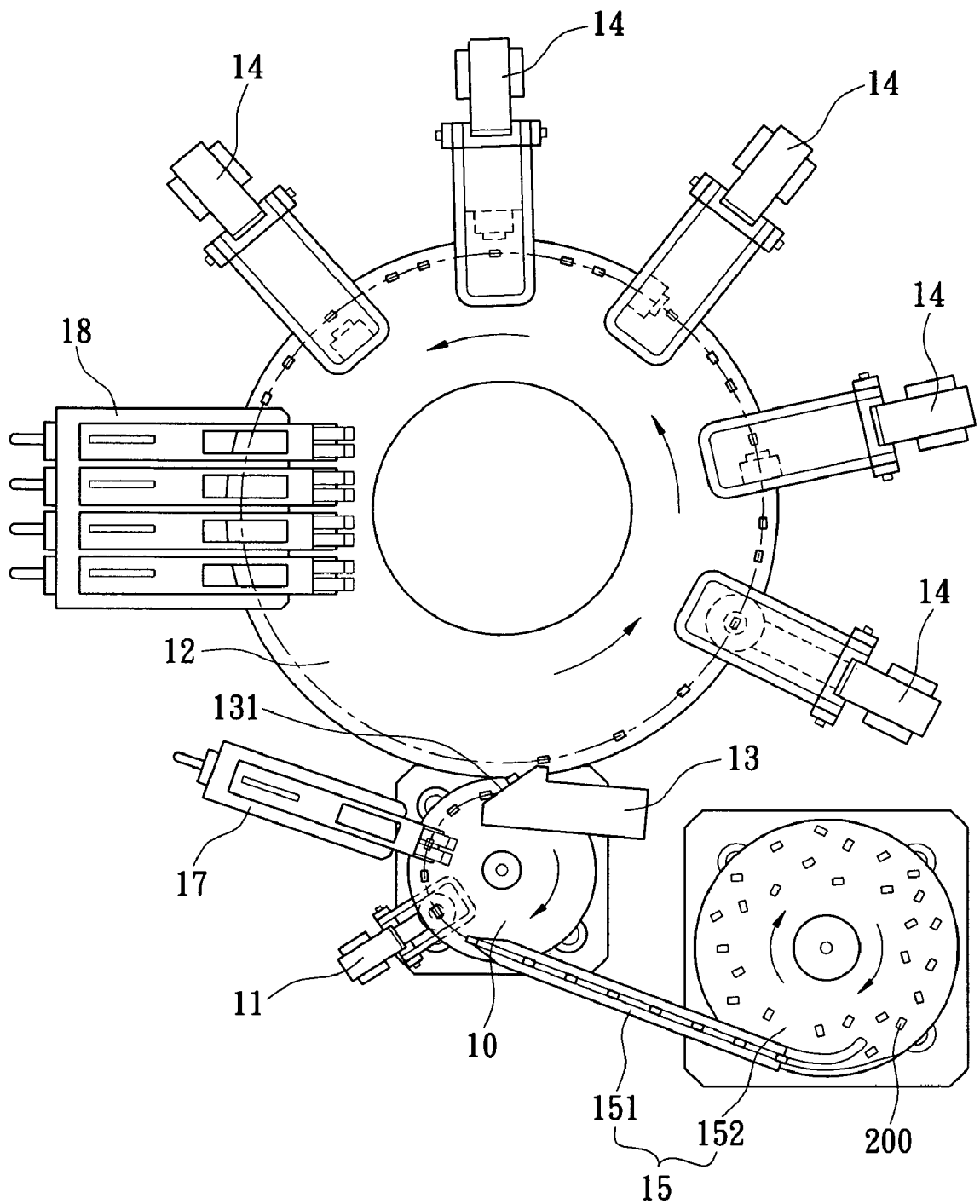
FIG. 1 shows the schematic view of the testing system for inspecting electronic devices according to the present invention.

Please refer to FIG. 1, the present invention discloses a testing system for inspecting the outlooks of a plurality of electronic devices 200. The testing system includes a first transparent disk 10 (a.k.a. small size disk), a first image capturing unit 11, a second disk 12, a guiding unit 13 and a plurality of second image capturing units 14. The first transparent disk 10 and the second disk 12 are used for carrying the electronic devices 200 thereon in order to inspect the surface images of each electronic device 200. Therein the first transparent disk 10 is used to inspect the bottom surface of the electronic devices 200, and the second disk 12 is used to inspect the other surfaces of the electronic devices 200. Therein, the other surfaces includes front surface F, rear surface R, top surface T, left surface LS, and right surface RS Please refer to FIG. 2, the first transparent disk 10 is made of quartz glass so that the first transparent disk 10 has a high degree of hardness. The first image capturing unit 11 is disposed under the first transparent disk 10. When the electronic devices 200 are continuously supplied on the rotating first transparent disk 10, each of the electronic devices 200 are then sequentially moving to a position which is above the first image capturing unit 11 so that the first image capturing unit 11 can capture the image of bottom surface B of each electronic device 200 (please refer to FIG. 3 for surface designation) though the first transparent disk 10. Therefore, the testing system can determine the quality of the electronic devices 200 by analyzing the bottom surface image of each electronic device 200. As mentioned above, the first transparent disk 10 made of quartz glass material and the high degree of hardness of the quartz glass prevents the first transparent disk 10 from being scratched by the electronic devices 200. However, the material applied for manufacturing the first transparent disk 10 is not restricted to quartz glass, but materials preferably have a high degree of hardness and transparency. A feeding unit 15 is used for sequentially and, continuously supplying the electronic devices 200 on the first transparent disk 10. The feeding unit 15 has a feeding disk 151 and at least one feeding track 152. The electronic devices 200 are lined up on the feeding disk 151 and then transferred onto the first transparent disk 10 via the feeding track 152.

The testing system has a second disk 12 disposed adjacently to the first transparent disk 10 and a guiding unit 13 disposed on the adjacent area between the first transparent disk 10 and the second disk 12. The electronic devices 200 whose bottom surface images are captured by the first image capturing unit 11 then moves onto the rotating first transparent disk 10, and then the electronic devices 200 are guided to be transferred onto the second disk 12 for inspecting their other surfaces (i.e. non-bottom surfaces). Because the two disks 10, 12 have circular arc-edge, there is a critical position on which the two disks 10, 12 are nearest yet still allows for the two disks 10, 12 to rotate, i.e., the distance W1 between the first transparent disk 10 and the second disk 12 on the critical position is smaller than distance on any other position provided that disks 10 and 12 are still free to rotate, and this W1 distance is also referred as smallest adjacent width. If W1 is preferably smaller than the width W of the electronic device 200 (shown in FIG. 3), and the guiding surface 131 of the guiding unit 13 is preferably located on the critical position with smallest adjacent width W1, then the electronic devices 200 will not fall though the gap between the first transparent disk 10 and the second disk 12 when the electronic devices 200 is being transferred form the first transparent disk 10 to the second disk 12 via the guiding surface 131 of the guiding unit 13. On the other hand, the distance W1 can be zero provided that the two disks can still rotate, i.e., the first transparent disk 10 contacts with the second disk 12 but both can still rotate. Preferably, the top surface of the second disk 12 is not higher than the top surface of the first transparent disk 10 so that the electronic devices 200 can be smoothly transferred from the first transparent disk 10 to the second disk 12. The second disk 12 is made of metal and the size of the second disk 12 is larger than the size of the first transparent disk 10. Due to the high price of quartz glass, the smaller size of the first transparent disk 10 is used for reducing the cost of manufacturing the testing system.

The second image capturing units 14 are applied for capturing the surface images including the images of front surface F, rear surface R, top surface T, left surface LS, and right surface RS. In the embodiment, the testing system has five second image capturing units 14 disposed around the second disk 12 and each second image capturing unit 14 can capture the corresponding image of the surfaces. Therefore, the testing system can determine the quality of the electronic devices 200 by analyzing the images of the above-described surfaces of each electronic device 200.

Figure 2:
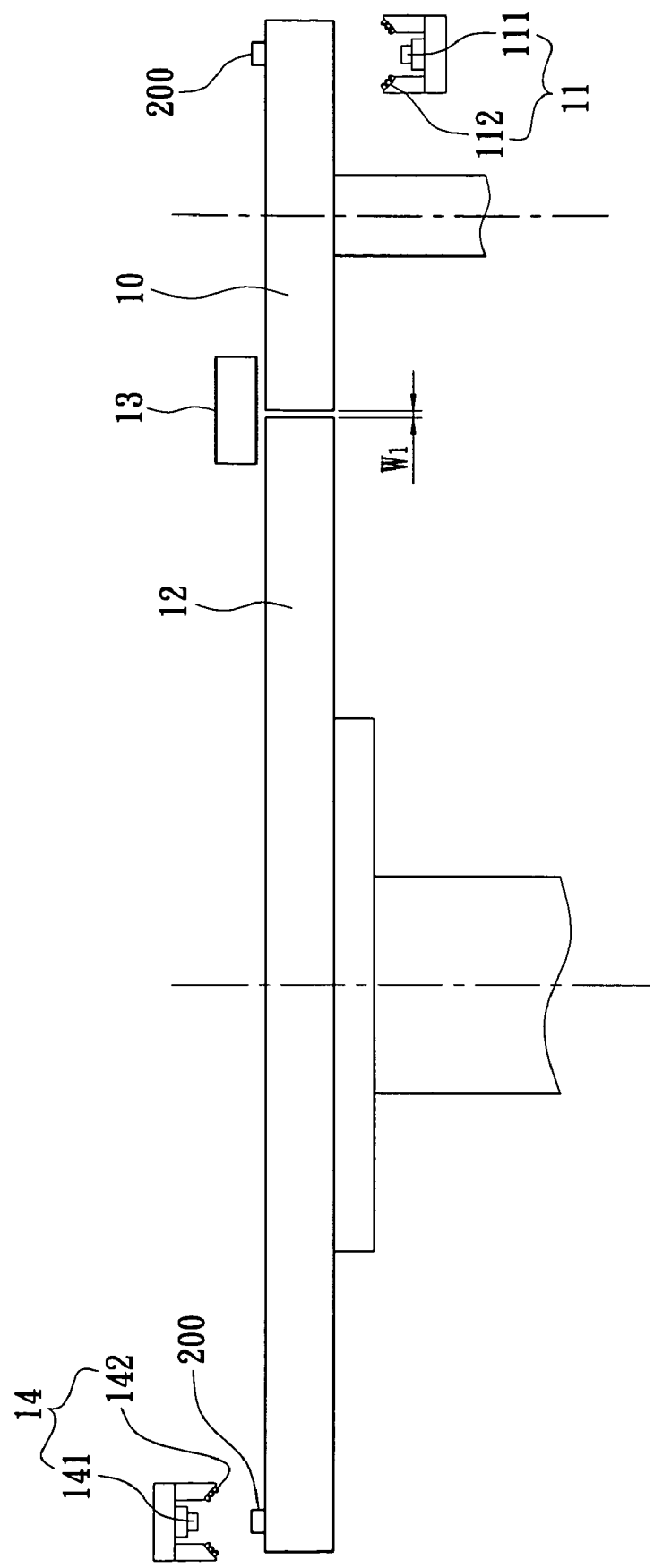
FIG. 2 is a side view showing the testing system for inspecting electronic devices according to the present invention.
Figure 3:
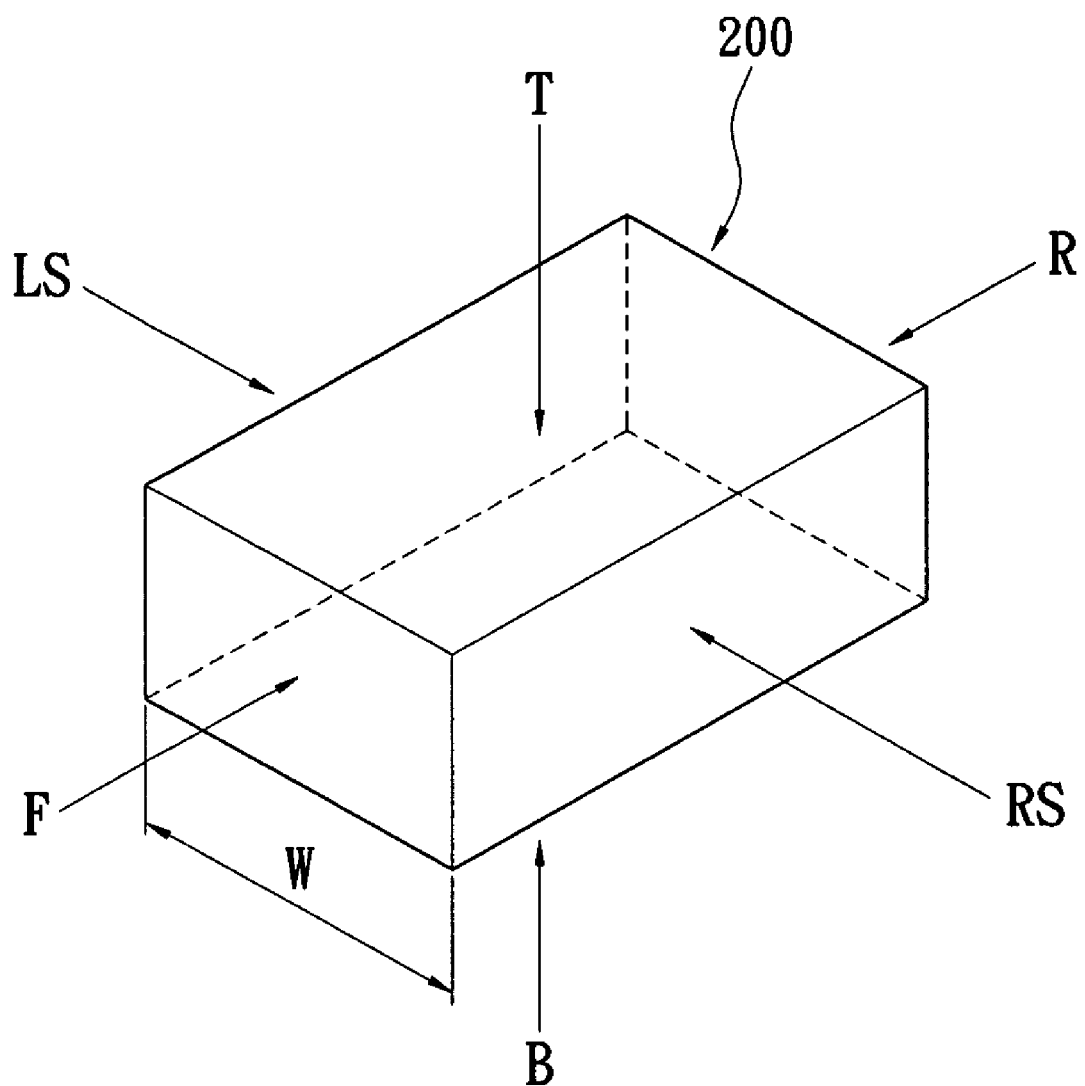
FIG. 3 is a schematic view showing the outlook of an electronic device.

The first and second image capturing units 11, 14 respectively have a camera and a plurality of lighting units cooperating with the camera. Please refer to FIG. 2, the first image capturing unit 11 is disposed under the first transparent disk 10 and has a first camera 111 and a first lighting units 112. The second image capturing units 14 are disposed above the second disk 12 (only one second image capturing unit 14 is shown in FIG. 2). Similarly, each second image capturing unit 14 has a second camera 141 and second lighting units 142. The first and the second lighting units 112 and 142 are, for example, light emitting diodes (LEDs) and they can project different lights with different intensity for different inspecting devices, or can adjust the angles of the light according to the position of the inspecting devices.

Figure 4:
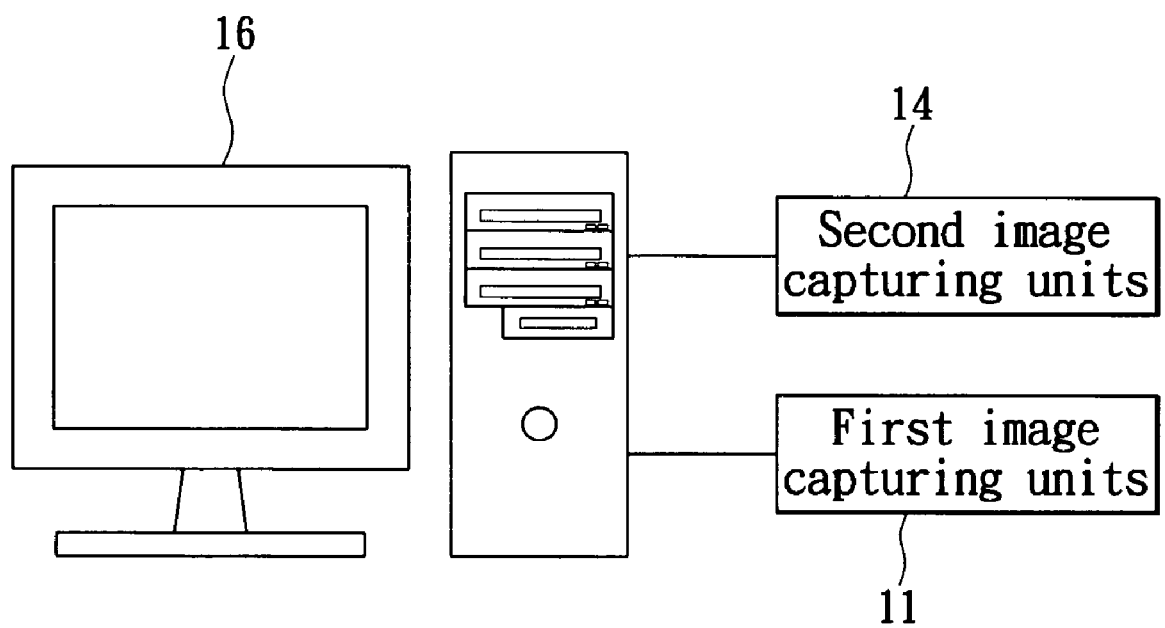
FIG. 4 shows the schematic view of the analysis and control unit in cooperation with the first and the second image capturing units according to the present invention.

Please refer to FIG. 4, the testing system further comprises an analysis and control unit 16 electrically connected to the first image capturing unit 11 and the second image capturing unit 14 and the analysis and control unit 16 is used for receiving and analyzing the bottom images of the electronic devices 200 captured by the first image capturing unit 11 and for receiving and analyzing the images of other surfaces of the electronic devices 200 captured by the second image capturing units 14. The analysis and control unit 16 also controls a first collection unit 17 and the second collection unit 18 to respectively collect the electronic devices 200 on the first transparent disk 10 and the second disk 12. In other words, the present invention provides a two-step inspection procedure with high testing efficiency. The high efficiency is due to the fact that once a defect is found on the bottom surface B of an electronic device 200, the electronic device 200 is deemed un-qualified, and the collection unit 17 would proceed and extract the un-qualified electronic device 200, which eliminated scanning and examination of the other surfaces of the un-qualified electronic device 200. The first step of the two-step inspection procedure includes that when the bottom image of the electronic devices 200 is captured by the first image capturing unit 11 and then analyzed and classified into un-qualified specie by the analysis and control unit 16, the un-qualified electronic devices 200 are removed form the first transparent disk 10 and collected by the first collection unit 17. Therefore, the un-qualified electronic devices 200 are not sent to the second disk 12 and the inspection efficiency is improved. Only qualified electronic devices 200 on the first transparent disk 10 are sent to the second disk 12 to inspect other surface images (i.e., the second step). Moreover, the electronic devices 200 are classified into qualified and un-qualified species by the second collection unit 18 controlled by the analysis and control unit 16.

Figure 5:
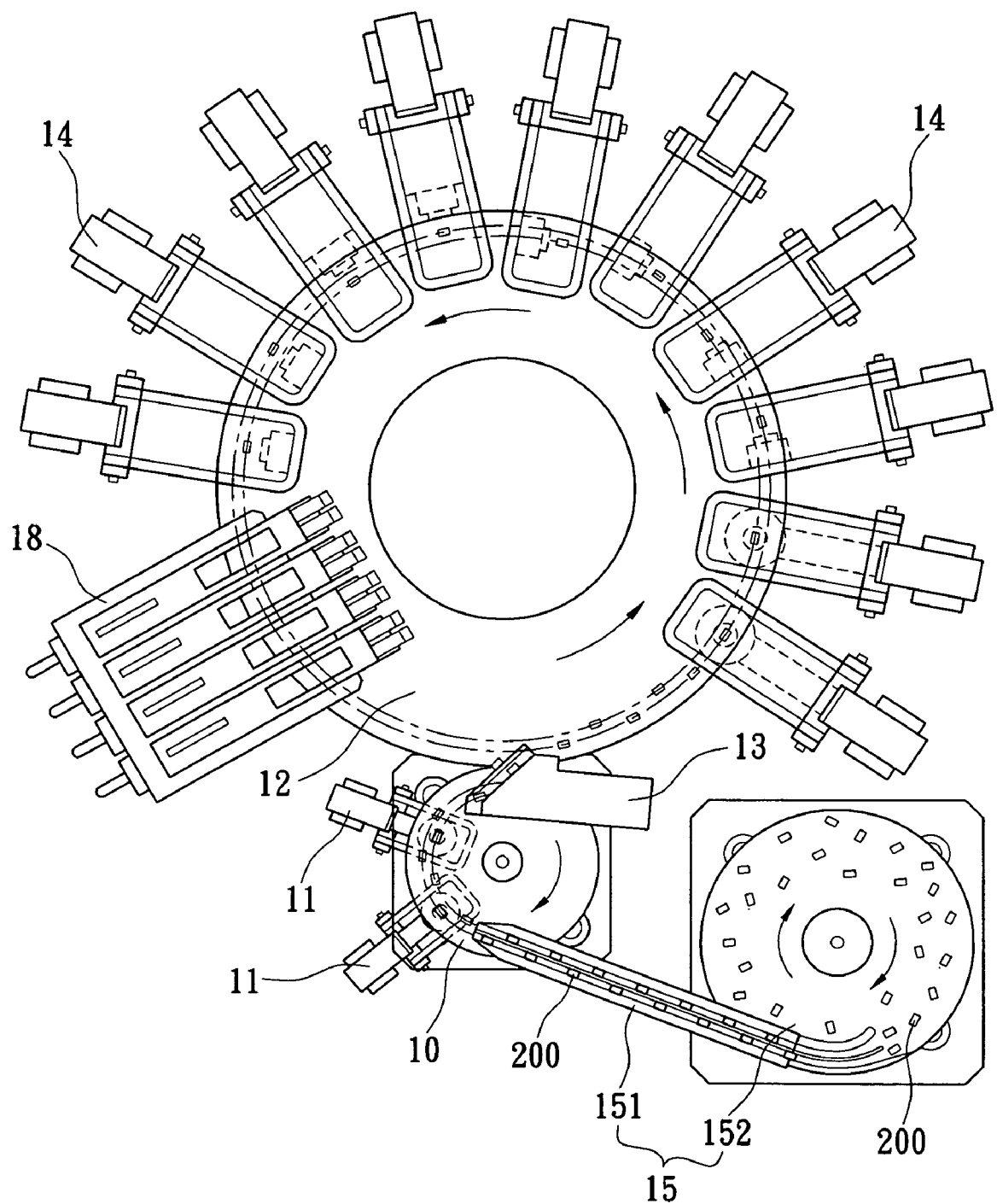
FIG. 5 shows the schematic view of the second embodiment of the testing system for inspecting electronic devices according to the present invention.

Please refer to FIG. 5, the second embodiment is shown. The feeding unit 15 can has a feeding disk 151 and two feeding tracks 152 and, the electronic devices 200 can be arranged in two lines to continue the inspection (i.e. 5 e second image capturing units 14 covering 5 surfaces of electronics devices 200 on one line, and the other 5 second image capturing units 14 covering 5 surface of electronics devices 200 on the other line). The number of image capturing units is different from the first embodiment, for example, there are ten second image capturing units 14 disposed near the second disk 12 for capturing the images of front surface F, rear surface R, top surface T, left surface LS, and right surface RS of the two lines of electronic devices 200.

Also, the positions of the first transparent disk 10 and the second disk 12 may be changed in another embodiment. In other words, the electronic devices 200 are first supplied on the second disk 12 for inspecting the images of front surface F, rear surface R, top surface T, left surface LS, and right surface RS of the electronic devices 200 and then be guided by the guiding unit 13 to transfer onto the first transparent disk 10 for analyzing the bottom surface image. Then finally, the electronic devices 200 are classified into qualified and un-qualified species.

Furthermore, the second disk 12 can have a plurality of surfaces in co-circle form, i.e., a multi-layer cake, and each of the surfaces is in accordance with a first transparent disk 10 and a guiding unit 13 to form as an inspection module. Thus, the inspection module can be used for inspecting the electronic devices 200 individually so that the testing system can used for inspecting many lines of the electronic devices 200 at the same time.

Accordingly, a testing method is disclosed for the testing system mentioned above. The testing method includes the following steps. Step (a) is continuously providing the electronic devices 200 on the first transparent disk. Step (b) using the first image capturing unit 11 to capture the bottom surface images of the electronic devices 200. Step (c) is transferring the electronic devices 200 from the first transparent disk 10 onto the second disk 12 via the guiding unit 13. Step (d) is using the second image capturing units 14 to capture the surface images including the images of front surface F, rear surface R, top surface T, left surface LS, and right surface RS of the electronic devices 200. A feeding step is provided before step (a) for sequentially and continuously supplying the electronic devices 200 on the first transparent disk 10. A first analyzing step for analyzing the bottom surface of each electronic device 200 after step (b) by an analysis and control unit 16 is further disclosed, and the analysis and control unit 16 is connected electrically to the first image capturing unit 11. Furthermore, a first collection step is executed after the first analyzing step for collecting the un-qualified electronic devices 200 by a first collection unit 17 which is controlled by the analysis and control unit 16. A second analyzing step for analyzing the image of the top surface T, the front surface F, the rear surface R, the right surface RS, and the left surface LS of each electronic device 200 is executed after step (d) and then the electronic devices 200 are collected in a second collection step by the second collection unit 18 which is controlled by the analysis and control unit 16.

To sum up, the present invention has following advantages.

1. The cost of the testing system is reduced. The first transparent disk 10 is made of quartz glass and is in smaller size; therefore, the problem of high price of quartz glass is solved.

2. Quartz glass and metal material both have a high degree of hardness so that the first transparent disk and the second disk are prevented from being scratched by the electronic devices. Therefore, the captured images are prevented from scattering effect of light resulting from the scratch so that the image analysis can be more precise.

3. A two-step inspection method is disclosed and the testing efficiency is improved.

Although the present invention has been described with reference to the foregoing preferred embodiment, it shall be understood that the present invention is not limited to the details thereof. Various equivalent variations and modifications may occur to those skilled in this art in view of the teachings of the present invention. Thus, all such variations and equivalent modifications are also embraced within the scope of the invention as defined in the appended claims.

What is claimed is:

1. A testing system for inspecting electronic devices, comprising:
    a first transparent disk, wherein the electronic devices are continuously supplied on the first transparent disk;
    a first image capturing unit disposed under the first transparent disk for capturing bottom surface images of the electronic devices;
    a second disk disposed adjacently to the first transparent disk;
    a guiding unit disposed on of an adjacent area between the first transparent disk and the second disk for transferring the electronic devices onto the first transparent disk to the second disk; and
    a plurality of second image capturing units disposed around the second disk for capturing images of other surfaces of the electronic devices.

2. The testing system according to claim 1, further comprising a feeding unit for sequentially and continuously supplying the electronic devices onto the first transparent disk.

3. The testing system according to claim 2, wherein the feeding unit has a feeding disk and at least one feeding track.

4. The testing system according to claim 1, wherein the smallest adjacent width between the first transparent disk and the second disk is equal or smaller than the width of each electronic device.

5. The testing system according to claim 1, wherein the first transparent disk is made of quartz glass and the second disk is made of metal materials.

6. The testing system according to claim 1, wherein a size of the first transparent disk is smaller than a size of the second disk.

7. The testing system according to claim 1, wherein the guiding unit has a guiding surface disposed on the adjacent area between the first transparent disk and the second disk, and the electronic devices are transferred from the first transparent disk onto the second disk via the guiding surface.

8. The testing system according to claim 1, further comprising an analysis and control unit for receiving and analyzing the bottom surface images of the electronic devices captured by the first image capturing unit and for receiving and analyzing the images of other surfaces of the electronic devices captured by the second image capturing units.

9. The testing system according to claim 8, further comprising a first collection unit disposed in close proximity to the first transparent disk, wherein the first collection unit is controlled by the analysis and control unit to collect the electronic devices.

10. The testing system according to claim 1, wherein each of the first image capturing unit and the second image capturing units has a camera and a plurality of lighting units.

11. A testing method for inspecting outlooks of electronic devices using a testing system, the testing system comprising a first transparent disk, a first image capturing unit, a second disk, a guiding unit, and a plurality of second image capturing units, the testing method comprising:

(a). continuously providing the electronic devices on the rotating first transparent disk;

(b) capturing a bottom surface image of each electronic device via the first image capturing unit;

(c) transferring the electronic devices onto the rotating second disk; and (d) capturing images of other surfaces of the electronic devices via the second image capturing unit.

12. The testing method according to claim 11, further comprising a feeding step for sequentially and continuously supplying the electronic devices onto the first transparent disk before step (a).

13. The testing method according to claim 11, further comprising a first analyzing step for analyzing the bottom surface of each electronic device after step (b).

14. The testing method according to claim 13, further comprising a first collection step after the first analyzing step.

15. The testing method according to claim 11, wherein the second image capturing units capture an image of the other surfaces, and the other surfaces comprising a top surface, a front surface, a rear surface, a right surface and a left surface of each electronic device in step (d).

16. The testing method according to claim 15, further comprising a second analyzing step for analyzing the top surface image, the front surface image, the rear surface image, the right surface image and the left surface image of each electronic device after step (d).

17. The testing method according to claim 16, further comprising a second collection step after the second analyzing step.

* * * * *